United States Patent [19]

Blankemeyer

[11] Patent Number: 5,459,070
[45] Date of Patent: Oct. 17, 1995

[54] APPARATUS FOR RAPID TOXICITY TESTING OF A LIQUID SAMPLE

[75] Inventor: James T. Blankemeyer, Stillwater, Okla.

[73] Assignee: Oklahoma State University, Stillwater, Okla.

[21] Appl. No.: 306,834

[22] Filed: Sep. 15, 1994

Related U.S. Application Data

[62] Division of Ser. No. 153,415, Nov. 15, 1993, Pat. No. 5,416,005.

[51] Int. Cl.$^6$ .............................. C12M 1/34; C12Q 1/02; G01N 21/64
[52] U.S. Cl. .................. 435/287.1; 435/808; 435/288.7; 422/64; 250/461.2
[58] Field of Search ................................. 435/4, 7.21, 29, 435/291, 808; 250/372, 461.2; 422/62, 64; 424/9; 436/172

[56] References Cited

U.S. PATENT DOCUMENTS

| | | | |
|---|---|---|---|
| 4,548,907 | 10/1985 | Seitz | 436/163 |
| 4,811,218 | 3/1989 | Hunkapiller | 364/413.01 |
| 4,977,325 | 12/1990 | Bowen | 250/461.2 |
| 5,042,494 | 8/1991 | Alfano | 128/665 |
| 5,094,944 | 3/1992 | Hayes | 435/29 |

OTHER PUBLICATIONS

Sanchez P., Toxicity Assessment of Industrial . . . Tox Assess. An Int J., vol. 3 55–80 (1988).
Montana V., Dual–Wavelength Ratiometric . . . Biochem 1989 28 4536–4539.

*Primary Examiner*—William H. Beisner
*Assistant Examiner*—Ralph Gitomer
*Attorney, Agent, or Firm*—Dougherty, Hessin, Beavers & Gilbert

[57] ABSTRACT

A toxicity testing assay wherein a test sample is prepared with electrochromic dye and a living organism of the cladoceran order or other test organisms, and the sample is irradiated with alternately blue and yellow light to excite fluorescence. The successive groups of fluorescent emissions are then viewed at 90° by a photomultiplier which develops equivalent alternate count outputs, and the count output is amplified and processed to develop data indicating (1) membrane potential of cells of the living organisms and (2) the total dye fluorescence which provides indication of deleterious effects to the organisms.

7 Claims, 1 Drawing Sheet

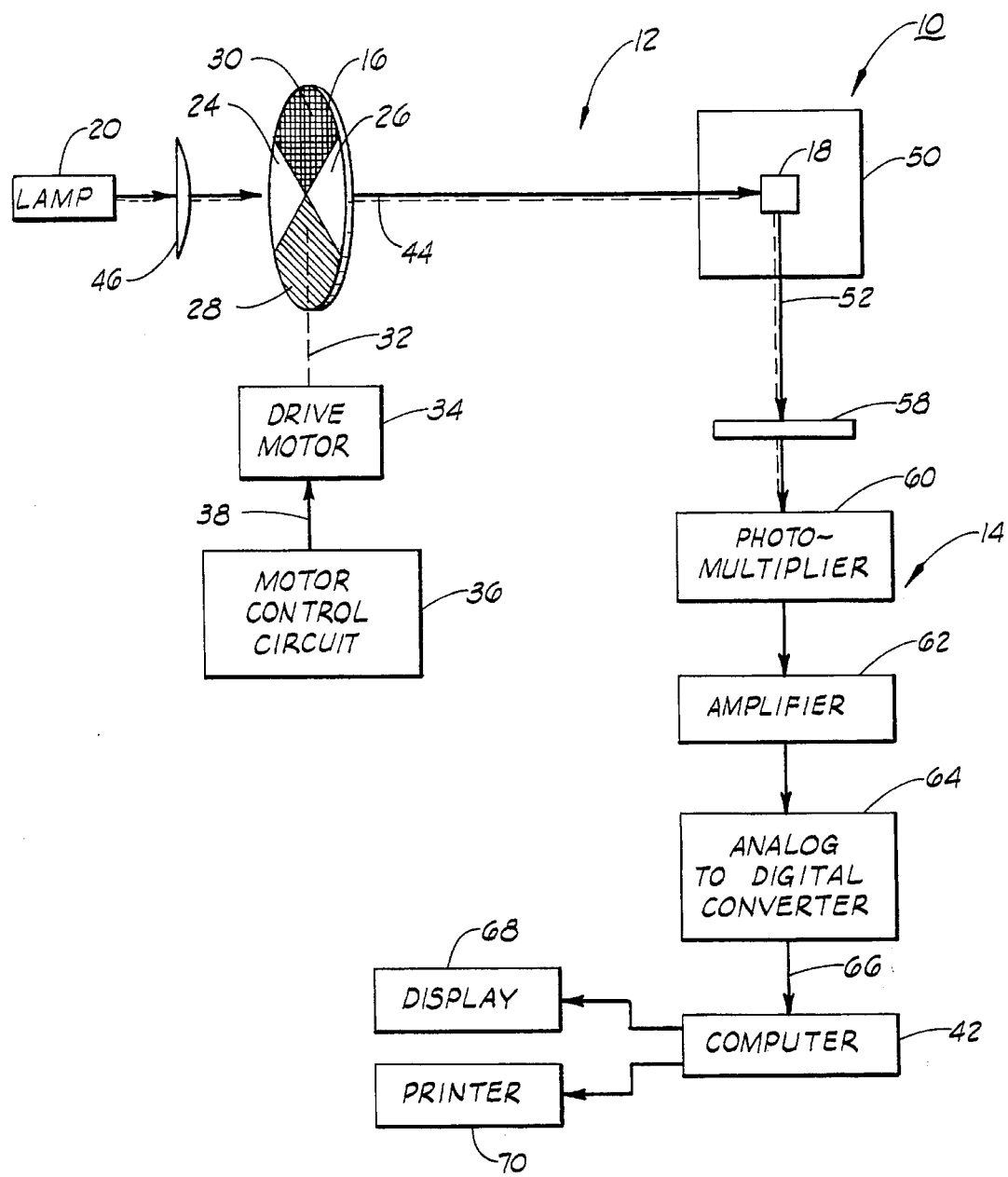

APPARATUS FOR RAPID TOXICITY TESTING OF A LIQUID SAMPLE

This application is a division of application Ser. No. 08/153,415 filed 11/15/93, now U.S. Pat. No. 5,416,005.

BACKGROUND OF THE INVENTION

1. Field of the Invention

The invention relates generally to aquatic toxicity testing and, more particularly, but not by way of limitation, it relates to improvements in both method and apparatus for toxicity testing liquid samples by quantifying the effects of the subject sample on Daphnia sp. or other aquatic species.

2. Description of the Prior Art

The prior art includes several types of testing methods for determining aquatic toxicity, and in most cases the prior methods attempt to derive a quantifiable result. A system known as chronic Whole Effluent Toxicity (WET) test is a relatively economical toxicity testing system that uses EPA-approved methods and test organisms; however, such a system has very limited portability and requires seven days to perform a single test. This biological test method uses representative organisms to estimate the effects of effluents discharged or receiving waters on the eco system.

Another assay system known as the MICROTOX® Toxicity Test utilizes the luminescent marine microorganisms which are altered as to light emission by changes in their metabolic processes. Reduction of light is proportional to toxicity of the sample. A testing reagent containing the microorganisms is freeze-dried for storage and is readily reconstituted for testing in a very short time. Finally, a toxicity test known as the IQ Test Kit™ provides a low price test system but one that does not produce quantifiable results. This test requires initial preparation of the test sample with organisms for subsequent irradiation in ultraviolet light (longwave). Acquired test data is then interpreted by means of other conventional assay methods.

SUMMARY OF THE INVENTION

The present invention relates to an improved type of toxicity test system that is able to rapidly produce quantitative/qualitative results. The present system is commercially termed "DAPHNIAQUANT™" and the system is designed to evaluate the deleterious effects on a selected organism(s) exposed to toxic substances such as impure water, sludge and the like. The condition of the organism will be reflected in the short-term alterations in the health of the cells that comprise the organism. The assay system functions to evaluate the membrane potential of cells of the affected organisms by using a voltage-sensitive dye, i.e., electrochromic, to optically transduce the membrane potential into fluorescent emissions. The fluorescent emissions are then photoelectrically detected and processed for input into an associated computer that is programmed to provide output of the requisite response in the form of quantitative/qualitative data.

The organisms having been subjected to the test sample are contained within a cuvette whereupon a light beam from a quartz-halogen lamp is temporally separated into distinct color bursts of alternate yellow and blue light beams for irradiation of the cuvette. The cuvette also contains a selected electrochromic dye which fluoresces in response to being illuminated with the alternate yellow and blue illumination to fluoresce at a selected frequency. The fluorescence is an indicator of the cell membrane potential (for blue light fluorescence) and the amount of dye that is fluorescing (for yellow light fluorescence). Analysis and plotting of a detected change in the fluorescence emission ratio from the two excitation colors then provides a quantified data output that is representative of the toxicity of the test sample.

Therefore, it is an object of the present invention to provide a toxicity testing system that is portable, lightweight and capable of conducting tests in minimal time.

It is also an object of the invention to provide such a toxicity test system that is capable of conducting a greater number of tests per unit time.

It is further an object of the present invention to provide a versatile system for optically measuring cellular characteristics of organisms by monitoring the response of an electrochromic dye thereby to provide data sufficient for toxicity testing, evaluating toxicity identification/reduction and the like.

Finally, it is an object of the present invention to provide a device for application in various toxicity identification and monitoring/assessment situations which is rapid and reliable in use while reducing overall testing costs.

Other objects and advantages of the invention will be evident from the following detailed description when read in conjunction with the accompanying drawing which illustrate the invention.

BRIEF DESCRIPTION OF THE DRAWING

The drawing figure is a functional block diagram of the assay system.

DETAILED DESCRIPTION OF THE INVENTION

The assay system of the present invention utilizes a specific test organism(s) in combination with selected fluorescent dye materials to provide the requisite indications. The test organisms may be living *Daphnia magna* or related organisms such as *Ceriodaphnia dubia, Ceriodaphnia affinis,* and *Daphnia pulex,* and there are a number of amphibian embryos and aquatic insects which might be used. These indicator test organisms are then placed in water of appropriate salinity and an electrochromic dye, Di-4-ANEPPS or Di-8-ANEPPS, is introduced into the prepared water. The dyes may be obtained commercially of proper purity and consistency, and each is actually an electrochromic fluorescing dye. The Chemistry Abstracts Registry Numbers and Names of the dyes are: Di-4-ANEPPS—90134-00-2 pyridinium, 4-[2-(6-dibutylamino)-2-naphthalenyl]ethenyl- 1(3-sulfopropyl)-, hydroxide, inner salt; and Di-8-ANEPPS is a new analog of D-4-ANEPPS not yet being assigned a Chemical Abstracts Registry name. The dyes have positive and negative charges such that the dye becomes interspersed in the organism membrane leaflet to effect changes in fluorescence directly in response to changes in membrane potential.

The Figure shows the assay system 10 which includes an illuminating section 12 and a processing section 14. The illuminating section 12 includes a rotating filter wheel 16 that provides successive, temporally separate color bursts which are then applied for examination of the sample within a cuvette 18, and output data is detected and processed in the processing section 14, as will be further described.

A quartz-halogen lamp 20, for example a 75 watt lamp of commercially available type, provides a non-collimated light beam 22 directed through an aspheric lens 46 which collects and collimates the light beam on an outer radial position of the filter wheel 16. Filter wheel 16 is an idealized representation illustrating the quadrature array of filter and opaque sections, i.e., opaque sections 24 and 26 disposed in opposite positions and a blue filter section 28 disposed opposite from a yellow filter section 30. The filter wheel 16 is rotated by a centrally-connected drive shaft 32 from drive motor 34 which receives drive energization from a motor control circuit 36.

The drive motor 34 may be such as a D-C motor that is commercially available as the Escap Type N28 available from the Portescap Corp. of New York, N.Y. The particular motor, Series 213E, is available and applied in a nine volt system. The drive motor 34 is energized by input from motor control circuit 36 which is a Motorola integrated circuit termed a Power Switching Regulator type MC 34166, and it is a free-running circuit that provides motor drive output on lead 38.

Thus, the filter wheel 16 is driven to provide alternating periods of blue and yellow light interspersed with periods of dark via a generally collimated beam 44. The light periods are divided into two specific wavelengths of filters which are integral with the filter wheel; the blue filter section 28 passes a blue light band that is centered at 470 nanometers, while the yellow filter section 30 passes a band that is centered at 580 nanometers.

The cuvette 18 is a clear glass, square container which is suitably held within a sample holder 50 in such position that it receives maximum illumination of the beam 48. The cuvette 18 contains the sample with a plurality of selected Daphnia species or other organisms swimming live therein, i.e., on the order of six to fifteen *Daphnia magna, Ceriodaphnia, Daphnia pulex*, or other selected organisms for which a standard has been established. Also, the electrochromic dye is added into the sample in an amount bringing it to a concentration of 1 mg/liter. Fluorescent emissions are detected along a line that is 90° from the incident beam 44. Thus, fluorescent emissions are apparent along a beam 52 through an interference filter 58 onto a photomultiplier 60. The interference filter 58 is selected for its ability to pass fluorescent emissions of a specific wave length, e.g., a pass band centered around 620 nanometers.

The detected emissive events are output from photomultiplier 60 as pulses which are input to an amplifier 62 and further input to an analog to digital converter 64. Digital pulse indications are then input via lead 66 to the computer 42 which is programmed to carry out the requisite processing to determine both (1) the membrane potential of the affected organism cells, and (2) the amount of dye that is fluorescing in total. Further, photoelectric count for the dark periods, i.e., during opaque filter sections 24 and 26 of filter wheel 16, provide a dark current indication from photomultiplier 60 which enables derivation of a background count that may be continuously subtracted from the succeeding fluorescence count data. The computer 42 may also include suitable peripherals such as display 68 and printer 70 which serve to indicate test results.

The test protocol for the assay system 10 is embodied in the software within computer 42. To begin analysis, the cuvette 18 is filled with the sample which is also infused with six to fifteen live Daphnia organisms, whereupon the commercial grade electrochromic dye is added to the sample, bringing the concentration to one milligram per liter. The dye enters into the plasma membrane of most of the cells of each of the organisms and the sample is ready for examination.

The lamp 20 is energized and drive motor 34 is brought up to proper speed to rotate the filter wheel 16 that produces an alternating illumination beam 44 having the characteristic of dark/yellow/dark/blue illuminations at a preselected repetition rate. As the alternating yellow and blue bursts of light in beam 44 enter the cuvette 18, they excite fluorescence which is apparent at a 90° angle along beam line 52 through an interference filter 58 onto the photomultiplier 60. The blue light photons entering cuvette 18, a light band centered at 470 nanometers, causes the cells of the organisms within cuvette 18 to emit a fluorescence that will be proportional to the membrane potential of those cells that contain the dye. The fluorescence will increase as the membrane potential hypopolarizes. A next successive burst of yellow light, in a band centered at 580 nanometers, will also illuminate the organisms, and the individual cell membranes containing the dye will fluoresce in proportion to the total amount of dye that is fluorescing as it is interspersed in the plasma membrane. That is, the dye fluoresces in proportion to the dye concentration and independent of the membrane potential.

The dark period between successive color bursts serves to provide a dark current reading from the photomultiplier 60, and this enables a background count to be established for continuous subtraction from the blue and yellow data counts. This subtraction can take place within computer 42 whereby digital values for each time period are derived from analog to digital convertor 64. Computer 42 subtracts dark current and cleans up the pulse counts for both blue and yellow filter periods. In processing, a complete photon count period may be on the order of twenty seconds with detection and storage of the blue and yellow pulse counts, whereupon the accumulated pulses are then analyzed to determine the quantity of fluorescence of the organisms within cuvette 18, and this count data is further stored in memory within computer 42.

After the incubation period of five to fifteen minutes, the membrane potential or blue light response of the cells within the organisms can be measured, summed, averaged and displayed or printed out on the display 68 and printer 70. Generally, the results of an assay test are a data stream of fluorescence versus time, and the data stream contains indication of the control with no toxic substance, and the effect of the toxic substance on the organisms.

A deleterious effect of the test sample on the test organism within cuvette 18 is detected by a change in the fluorescent emission, i.e., change in ratio, as between the two excitation colors, blue and yellow. Most compounds will cause an increase in fluorescence termed a hypopolarization, however, some compounds such as the aqueous organics will cause a hyperpolarization. This change in membrane potential occurs rapidly, within five minutes for many compounds. Any change in membrane potential due to toxicity in the sample as measured by the fluorescence of the dye follows a concentration-response relationship. That is, larger concentrations of toxicant in the sample produces larger responses in direct proportion, and this property allows comparison of relative toxicity as between differing sample lots.

The foregoing discloses a novel form of assay testing system for quantitative/qualitative toxicity testing using test organisms from the Daphnia species and other organisms. The system derives cellular indications of the health of the test organism and by so doing it can rapidly predict the assay result. The assay system is able to utilize optical measurements of cellular characteristics of the organisms, and measurements are performed during a predetermined time exposure using fluorescent dyes in order to quantify the response to toxicants. The assay system of the present invention is reliable and user-friendly, and the instrument is sufficiently compact and light in weight that portable, battery-powered units may be employed and used with compact, lap-top computers at any selected site. The assay system is extremely versatile as it may be employed for toxicity source identification, storm water toxicity monitoring, ground water toxicity assessment, rapid, pure compound toxicity testing, or adaptation to any of a number of toxicity testing modes or environments.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. Apparatus for testing the toxicity of a liquid sample, comprising:

a transparent sample holder for containing the liquid sample, an amount of D-4-ANEPPS which is a dialkylaminostyrl pyridinium sulfonate dye, and a plurality of living organisms of the daphnia species which includes *Daphnia magna, Ceriodaphnia dubia, Ceriodaphnia affinis*, and *Daphnia pulex;* a lamp providing a beam of light directed at said sample holder;

a filter wheel means intercepting said beam of light periodically and alternately with a blue light filter centered at 470 nanometers and a yellow light filter centered at 580 nanometers;

light transmission means directed at said sample holder ninety degrees removed from the beam of light from said lamp to transmit fluorescent emissions;

a photomultiplier for detecting first fluorescent emissions at 620 nanometers in response to blue light and second fluorescent emissions at 620 nanometers in response to yellow light, and providing first and second count outputs; and data processing means for identifying the first count output occurring during operation of the blue light filter to quantify the living organism membrane potential, and for identifying the second count output occurring during operation of the yellow light filter to quantify total dye fluorescence, and including means for indicating the first and second count outputs over a predetermined time interval whereby a change in a ratio of the first count output and the second count output is a measure of toxicity of the liquid sample.

2. Apparatus for testing as set forth in claim 1 wherein said light transmission means includes:

an interference filter passing light having a passband centered at 620 nanometers from said sample holder.

3. Apparatus for testing as set forth in claim 1 wherein said filter wheel means comprises:

a wheel having quadrature sectors consisting of opposed opaque sectors and opposed blue light and yellow light filter sectors; and drive means for rotating said wheel.

4. Apparatus for testing as set forth in claim 3 which further includes:

a motor control circuit providing input pulse timing to each of said drive means and said data processing means.

5. Apparatus for testing as set forth in claim 1 which further includes:

means for detecting dark current indication during periods between blue light and yellow light illuminations to enable background correction of the respective first and second count outputs.

6. Apparatus for testing the toxicity of a liquid sample, comprising:

a transparent sample holder for containing the sample, an amount of 8-Di-ANEPPS which is a dialkylaminostyrl pyridinium sulfonate dye, and a plurality of living organisms of the daphnia species which includes *Daphnia magna, Ceriodaphnia dubia, Ceriodaphnia affinis*, and *Daphnia pulex;* a lamp providing a beam of light directed at said sample holder;

a filter wheel means intercepting said beam of light periodically and alternately with a blue light filter centered at 470 nanometers and a yellow light filter centered at 580 nanometers;

light transmission means directed at said sample holder ninety degrees removed from the beam of light from said lamp to transmit fluorescent emissions;

a photomultiplier for detecting first fluorescent emissions at 620 nanometers in response to blue light and second fluorescent emissions at 620 nanometers in response to yellow light, and providing first and second count outputs; and data processing means for identifying the first count output occurring during operation of the blue light filter to quantify the living organism membrane potential, and for identifying the second count output occurring during operation of the yellow light filter to quantify total dye fluorescence, and including means for indicating the first and second count outputs over a predetermined time interval whereby a change in a ratio of the first count output and the second count output is a measure of toxicity of the liquid sample.

7. Apparatus for testing as set forth in claim 6 which further includes:

means for detecting dark current indication during periods between blue light and yellow light illuminations to enable background correction of the respective first and second count outputs.

* * * * *